United States Patent [19]

Zdanevitch et al.

[11] Patent Number: 5,709,792
[45] Date of Patent: Jan. 20, 1998

[54] METHOD OF CHARACTERIZING A GAS MIXTURE BY CATALYTIC OXIDATION

[75] Inventors: Isabelle Zdanevitch, Paris; Gérard Rose, Villers-Saint-Paul, both of France

[73] Assignee: Institut National de l' Environnement Industriel ET des Risques, France

[21] Appl. No.: 619,154

[22] Filed: Mar. 21, 1996

Related U.S. Application Data

[63] Continuation of Ser. No. 413,255, Mar. 30, 1995, abandoned.

[30] Foreign Application Priority Data

Mar. 31, 1994 [FR] France ................................. 94 03825

[51] Int. Cl.$^6$ ................................................. G01N 27/26
[52] U.S. Cl. ........................ 205/775; 205/787; 73/23.31; 436/141
[58] Field of Search ........................ 422/83, 88, 94, 422/95, 96, 97, 98; 73/23.31, 23.35, 23.34; 436/143, 141; 204/153.1, 153.2

[56] References Cited

U.S. PATENT DOCUMENTS

| | | | |
|---|---|---|---|
| 4,804,632 | 2/1989 | Schuck et al. | 422/97 |
| 5,070,721 | 12/1991 | Tantram | 422/94 |
| 5,234,737 | 8/1993 | Accorsi et al. | 422/94 |

FOREIGN PATENT DOCUMENTS

| | | |
|---|---|---|
| 0234251 | 9/1987 | European Pat. Off. . |
| 0444753 | 10/1991 | European Pat. Off. . |
| 0458058 | 11/1991 | European Pat. Off. . |
| 9012313 | 10/1990 | France . |

*Primary Examiner*—Bruce F. Bell
*Attorney, Agent, or Firm*—Vanophem Meehan & Vanophem, P.C.

[57] ABSTRACT

For identifying one of a plurality of known gases in a gaseous mixture based on air a single catalytic transducer is placed in the gaseous medium. The catalytic transducer is heated to a lower threshold temperature at which the oxidizable gas is oxidized little or not at all and a first value of a parameter characteristic of the thermal state of the transducer is captured. The catalytic transducer is then heated to an upper threshold temperature at which the oxidizable gas oxidizes significantly in contact with the catalytic transducer and a second value of the parameter characteristic of the thermal state of the transducer is captured. Using a predetermined law, a response signal representative of the gaseous medium is produced from the difference between the second and first values of the parameter characteristic of the thermal state of the catalytic transducer. The catalytic transducer is allowed to cool below the lower threshold temperature and the above operations are repeated cyclically.

14 Claims, 3 Drawing Sheets

METHOD OF CHARACTERIZING A GAS MIXTURE BY CATALYTIC OXIDATION

This is a continuation of application Ser. No. 08/413,255, filed Mar. 30, 1995, now abandoned.

BACKGROUND OF THE INVENTION

1. Field of the invention

The invention concerns a method of characterizing a gaseous mixture of air and at least one combustible gas or vapor by catalytic oxidation.

2. Description of the Prior Art

It is directed to a method of:

volumetric analysis of an air/combustible gas mixture with the accuracy required by metrology standards covering equipment for detecting and measuring combustible gases, resolving doubt for some mixtures, and/or identifying a gas.

The intended applications of the method include the following devices:

doubt resolving methane meter conforming to European metrology standard EN 50 055, explosion meter conforming to European metrology standard EN 50 057, multigas equipment conforming to European metrology standards EN 50 055 and EN 50 057 and identifying the gas whose volume concentration is measured, selective methane meter.

The influencing parameters operating on a catalytic transducer are the disturbing parameters to which the catalytic transducer is sensitive and to which its response is added algebraically to the response due to the gas, which introduces an error into the determination of the volumetric analysis. The main two influencing parameters are the thermal conductivity and the temperature of the gaseous mixture which determine heat losses from the transducer in the mixture.

At present, catalytic sensors always include a detector (the catalytic transducer) and a compensator.

The detector is heated to a temperature sufficient to oxidize all the gases. The heat released by the reaction of oxidation of the gas on the detector is measured by any technique. For example: measurement of the increase in the electrical resistance of the transducer (which is a function of its temperature)—or measurement of the decrease in the heating current if the transducer is operated at constant temperature.

The detector therefore gives a response to the variation of heat: variation due to oxidation of the gas—variation due to modification of losses in the mixture—variation due to the increase in the normal operating temperature for given electrical conditions, which can occur in the long term if the transducer is a filament which wears away.

The response signal from the detector $S_d$ is the algebraic sum of various signals: signal $S_T$ induced by the operating temperature—signal $S_p$ induced by the losses in the mixture—signal $S_g$ induced by oxidation of a gas: $S_d = S_T + S_p + S_g$.

As its name indicates, the function of a compensator is to compensate for the influence of these disturbing parameters on the response of the detector. Its geometry and its construction are identical to those of the detector with the result that it has the same temperature coefficient and the same wear coefficient. However, it has been subjected to a surface treatment which prevents the oxidation reaction from occurring. It is heated to the same temperature as the detector.

Its response signal $S_c$ is therefore: $S_c = S_T + S_p$.

The gas signal is obtained by subtracting the compensator signal from the detector signal. The subtraction is performed by any electric circuit: Wheatstone bridge, differential amplifier, etc. $S_d - S_c = S_g$.

As a general rule, the response signal represents the instantaneous value of a parameter characteristic of the thermal state of the catalytic detector or transducer.

In theory, the response of a catalytic transducer is not on a one-to-one basis. It increases up to the stoichiometric concentration of the gas in the medium (for which the quantity of oxygen in the mixture is just that required to oxidize all of the gas) and then decreases due to lack of oxygen to cancel out at 100% gas. The response is therefore ambivalent and there is some doubt as to the volumetric analysis that has to be resolved (hence the expression "doubt resolving").

Present day measuring devices are not able to resolve the doubt, but they lock the reading and the alarm if the concentration exceeds a fixed threshold below the stoichiometric concentration (i.e. they lock the reading on this threshold value and continue to give the alarm even if the response of the transducer subsequently drops below the threshold). Before releasing the reading and the alarm, the user must measure the concentration with another device of a different type (for example an instrument which determines the volume concentration from the measured conductivity of the mixture), or at the very least using a different detector operating under different conditions.

As far as we are aware, identification of a gas in air has never been achieved in this type of device, although it would, among other things, universalize the response of an explosion meter.

International Publication WO-A 90 12313 proposes pseudo-continuous feeding of a single catalytic filament for determining the concentration of a given gas, with a view to reducing electrical power consumption; the intention is to use the time to reach equilibrium to characterize the gas concerned. There is no provision for resolving doubt. European Patent 0 234 251 provides two alternative measurement modes each using a specific temperature for measuring the concentration of a given gas using a single filament: either measurement of the thermal conductivity at a low temperature if the concentration is high, or catalytic measurement at a high temperature if the concentration is low. Finally, European Patent 0 234 258 uses the combination of a detector filament and a compensator filament. These documents do not disclose simultaneous accurate measurement using a single filament (allowing for any spurious phenomena), resolution of doubt and identification of the gas in question.

An object of the invention is to alleviate the above drawbacks and to provide a method of characterizing a gaseous medium comprising mostly air and a lesser proportion of at least one oxidizable gas, using only a catalytic transducer with no compensator, which can determine the volume concentration of the medium of at least one predetermined oxidizable gas, which can also, still with a single transducer, resolve doubt in the case of some gases (especially methane) in conjunction with, still with a single catalytic transducer, optional simultaneous determination of the concentration in the medium of a plurality of predetermined oxidizable gases (and therewith at least the possibility of identifying the (supposedly single) gas of a plurality of predetermined gases which is present in the medium in addition to the air), this method being simple to use and reliable and having a moderate response time (typically in the order of a few seconds at most).

SUMMARY OF THE INVENTION

The invention is a method of identifying one of a plurality of known gases in a gaseous mixture based on air, wherein:

a single catalytic transducer is placed in the gaseous medium, the catalytic transducer is heated to a lower threshold temperature at which the oxidizable gas is oxidized little or not at all, and a first value of a parameter characteristic of the thermal state of the transducer is captured, then the catalytic transducer is heated to an upper threshold temperature at which the oxidizable gas oxidizes significantly in contact with the catalytic transducer and a second value of the parameter characteristic of the thermal state of the transducer is captured, using a set or predetermined law, a response signal representative of the gaseous medium is produced from the distance between the second and first values of the parameter characteristic of the thermal state of said catalytic transducer, the catalytic transducer is allowed to cool below the lower threshold temperature and the above operations are repeated cyclically.

The main innovative feature of the method is that it achieves all these results using the response of a single catalytic transducer, without using any other transducer or compensator to compensate for the influencing parameters.

The method as defined above thus entails measuring the response of the transducer for various increasing operating temperatures during a short heating phase and then, from these responses, and depending on the application, calculating the volume concentration, resolving the doubt and/or identifying the gas or gases. The duration of the extinction phase between the heating cycles is chosen according to the required response time for the intended application. The number of constant temperature phases, which determine the duration of the heating phase, also depends on the application: two such phases for a methane meter, up to five (or even more) such phases for the other two applications mentioned hereinabove.

The method can use all types of catalytic transducers but in practice it is particularly beneficial (where a rapid response is required) using transducers whose thermal inertia is sufficiently low to enable a short heating time. In this regard, filament type transducers are very suitable: pure platinum filaments or certain filaments covered with a catalyst material.

In accordance with preferred features of the invention, some of which may be combinable with others:

the catalytic transducer includes a resistive element and the catalytic transducer is heated to the lower threshold temperature and then to the upper threshold temperature by application of an electric current to the resistive element, the lower threshold temperature is close to the temperature above which the oxidizable gas begins to oxidize, the catalytic transducer is a platinum filament and the upper and lower threshold temperatures are such that the difference between them is at least equal to approximately 50° C. and at most equal to approximately 300° C. and is preferably at most equal to approximately 200° C., the predetermined oxidizable gas is methane, the response signal is either a signal dependent on the difference between the second and first values of the characteristic parameter if their difference is positive or a predetermined saturation signal if the difference is negative, the threshold temperatures are approximately 800° C. and approximately 1,000° C. if the catalytic transducer is a platinum filament and if the oxidizable gas is either methane or ethylene, the threshold temperatures are approximately 300° C. and approximately 600° C. if the catalytic transducer is a platinum filament and if the oxidizable gas is propane, butane or ethyl alcohol, the threshold temperatures are approximately 100° C. and approximately 200° C. if the catalytic transducer is a platinum filament and if the oxidizable gas is hydrogen, for characterization of the air-based gaseous medium for at least a second oxidizable gas having an oxidation onset temperature substantially different from that of the first gas, a lower threshold temperature is chosen for the second oxidizable gas at which the second oxidizable gas oxidizes little or not at all and an upper threshold temperature is chosen for the second oxidizable gas at which the second oxidizable gas oxidizes significantly, the threshold temperatures defining a temperature range substantially non-contiguous with, but optionally adjacent to, the threshold temperature range chosen for the first gas, the catalytic transducer is heated to the threshold values in succession, in increasing order, the instantaneous value of the parameter characteristic of the thermal state of the transducer is captured for each of the threshold temperatures, and a predetermined procedure is used to produce a global response signal from the differences between the values captured for the threshold temperatures of each gas, the temperature ranges are adjacent, for characterization of the gaseous medium for hydrogen and/or a gas chosen from ethyl alcohol, butane and propane, and/or a gas chosen from methane and ethylene, the catalytic transducer is heated successively to approximately 100° C., approximately 200° C., approximately 300° C., approximately 600° C., approximately 800° C. and approximately 1,000° C. and the global response signal is derived from the greatest difference, allowing for a characteristic constant, between values captured for each of the ranges between the aforementioned temperatures, for selective characterization of methane in other oxidizable gases in the gaseous medium the catalytic transducer is heated successively to approximately 100° C., approximately 200° C., approximately 300° C., approximately 600° C., approximately 800° C. and approximately 1,000° C. and the global response signal is produced from the difference, allowing for a characteristic constant, between the values obtained for 1,000° C. and 800° C., respectively, if the difference is significantly negative, or is greater than the differences obtained, allowing for the characteristic constants, for the other temperature ranges.

When the catalytic transducer is a platinum filament, the temperatures concerned are in practice the central temperatures, calculated from the measurements obtained by means of optical pyrometry, for example.

Objects, features and advantages of the invention emerge from the following description given by way of non-limiting example with reference to the appended drawings.

DETAILED DESCRIPTION OF THE PREFERRED EMBODIMENT

Figure 1:
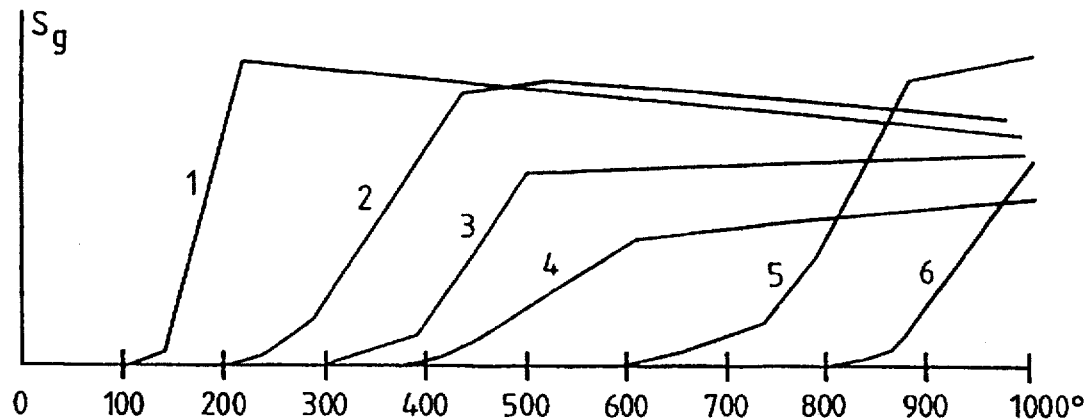
FIG. 1 is a graph showing the response of a given catalytic transducer for six different oxidizable gases for the same volume concentration (for example 1%)

FIG. 1 shows the response of a platinum filament for various oxidizable gases, as a function of its operating temperature. If the gas is methane (curve 6) and the filament is a coil of 80 μm diameter pure platinum wire, the order of magnitude of the response signal of the filament to the gas at 1,000° is 20 mV/%.

Below 800° the quantity of methane oxidizing on the filament is not sufficient to give a usable response. A usable response is obtained only above this temperature, and is then proportional to the temperature.

The gases to which FIG. 1 refers are:

1: hydrogen,
2: ethyl alcohol,
3: butane,
4: propane,
5: ethylene,
6: methane.

However, it must be understood that this is merely an illustrative list and that what follows is valid for many other oxidizable gases.

The theory of the method is based on the shape of these response characteristics and how they are offset as a function of temperature.

Volumetric analysis of a gaseous mixture based on air and in which a single given oxidizable gas may be present entails three steps:

at time t1 the filament is heated to the lower threshold temperature T1 (chosen so that the given gas oxidizes little or not at all—this temperature is preferably close to the temperature at which this gas begins to oxidize) and gives a response signal S1 which is a function of: T1—thermal losses in the mixture—quantity of gas oxidized, $$S1 = S_T1 + S_p1 + S_g1$$

at time t2 the filament is heated to the upper threshold temperature T2 (greater than T1) and gives a response signal S2:

$$S2 = S_T2 + S_p2 + S_g2$$

at time t3 heating of the filament is stopped. The concentration of the gas can be determined from the measured values S1 and S2 in two ways, depending on the hypotheses adopted.

A simplified method assumes that the terms $S_p2$ and $S_p1$ are practically equal (if the two operating temperatures are sufficiently close together) with a difference in the order of 100° C. to 200° C., for example.

This simplified method uses the difference:

$$d1 = S2 - S1 - Ct1$$

where Ct represents the term $S_T2 - S_T1$. This term is calculated and stored by the instrument during zero adjustment in clean air (air containing no combustible gas). Note that the value of $S_T2 - S_T1$ remains constant even as the filament wears away: wearing of the filament causes its resistance to increase, which shifts $S_T2$ and $S_T1$ in the same positive sense by amounts which are sufficiently similar for the resulting error to remain within metrology tolerances.

Consequently:

$$S2 - S1 - Ct = S_g2 - S_g1$$

which yields, if there is no oxidation of the gas at T1:

$$d1 = S_g2$$

Another, more accurate method requires a greater number of parameters to be determined beforehand by experiment. To allow for the fact that the terms $S_p2$ and $S_p1$ are not in fact equal, the following magnitudes can be used:

$$\Delta S2 = S2 - S2_0$$

$$\Delta S1 = S1 - S1_0$$

where $S1_0$ and $S2_0$ are measured values obtained at temperatures T1 and T2 in clean air (in practise they must be measured again at regular intervals if the transducer is a filament subject to wear).

Thus, substituting for S1 or S2, or $S1_0$ or $S2_0$:

$$\Delta S2 = (S_p2 - S_p2_0) + (S_T2 - S_T2_0) + (S_g2 - S_g2_0)$$

which, since the second term is a null term and by definition $S_g2_0$ is null, gives:

$$\Delta S2 = (S_p2 - S_p2_0) + S_g2 = S_p2 + S_g2$$

where the symbol Δ designates a difference.
Likewise:

$$\Delta S1 = \Delta S_p1 + S_g1$$

A coefficient K1 is defined by the equation:

$$\Delta S_p2 = K1 . \Delta S_p1$$

and can be assumed to be constant for any given pair T1, T2 regardless of the concentration of combustible gas (assumed to be low); it can therefore be easily determined in advance.

The term:

$$d'1 = \Delta S2 - K1 . \Delta S1$$

can be written:

$$d'1 = S_g2 - K1 . S_g1$$

This expression is slightly more complex than the expression given above for d1.

However, d'1 has the same physical meaning as d1 if T1 is such that the gas is not oxidized, that is:

d'1=$S_g$2

The choices of T1 and T2 and the difference between them determine the sensitivity of the sensor and its stability (which is improved by this method). The sensitivity is the amplitude of the response signal per percentage point of the volume concentration of oxidizable gas (V/%). Stability means maintained performance in time. If T2−T1 decreases, the sensitivity decreases but the stability increases.

As the response of a catalytic detector as a function of its operating temperature is different depending on the gas concerned, a volume concentration can be calculated for a gaseous medium containing a plurality of gases (having curves which are clearly offset as a function of temperature) from response signals for two temperatures only. For example, FIG. 1 shows that it is impossible to determine the concentration of gases 1, 2, 3 and 4 using the temperatures required to determine the concentration of gases 5 and 6 (in practice 900° C. and 1,000° C.).

For the purposes of characterization (identification of one of several known gases likely to be present in the gaseous medium (explosion meter)), a plurality of constant temperature phases in increasing temperature order are required, together with a pair of threshold temperature values for determining the concentration of a gas or a set of gases for which the sensor can yield a specific response:

100° C. and 200° C. for gas 1

300° C. and 600° C. for gas 2, 3 or 4

800° C. and 1,000° C. for gas 5 or 6.

The method is then as follows:

at time t1 the detector is heated to the operating temperature T1 at which there is no significant oxidation of any of the gases; the response signal S1 of the detector is measured and stored;

at time t2 the detector is heated to temperature T2 at which only one of the gases can oxidize; the response signal S2 of the detector is measured and stored;

at time t3 the detector is heated to temperature T3 at which only one further gas is able to oxidize; the response signal S3 of the detector is measured and stored;

at time tn the detector is heated to temperature Tn; the response signal Sn of the detector is measured and stored;

at time t(n+1) heating of the detector is stopped.

The next step depends on the method chosen; if the simplified method is used the following differences are established:

$d(n-1)=Sn-S(n-1)-Ct(n-1)$

. . .

$d3=S4-S3-Ct3$ $d2=S3-S2-Ct2$ $d1=S2-S1-Ct1$

The greatest result gives the volume concentration, subject to a sensitivity coefficient (which can be determined by calibration); the constants Ct(n−1) through Ct1 are determined beforehand and stored by the instrument during zero adjustment in clean air.

Note that the method as described so far concerns contiguous ranges, meaning that the upper threshold temperature of one range is the lower threshold temperature of the next higher range. As an alternative to this, the ranges for which the difference d is of interest can be non-contiguous.

Since the characteristic curve of the gases varies little and in a continuous (and known) manner beyond their maximum, the above considerations can be generalized to the identification and simultaneous determination of volume concentration of several gases in air, especially if the temperature ranges containing the steeply ascendant segments of the curves of these gases are substantially non-contiguous.

The doubt can be resolved with a gas such as methane having a thermal conductivity greater than that of air.

Figure 2:
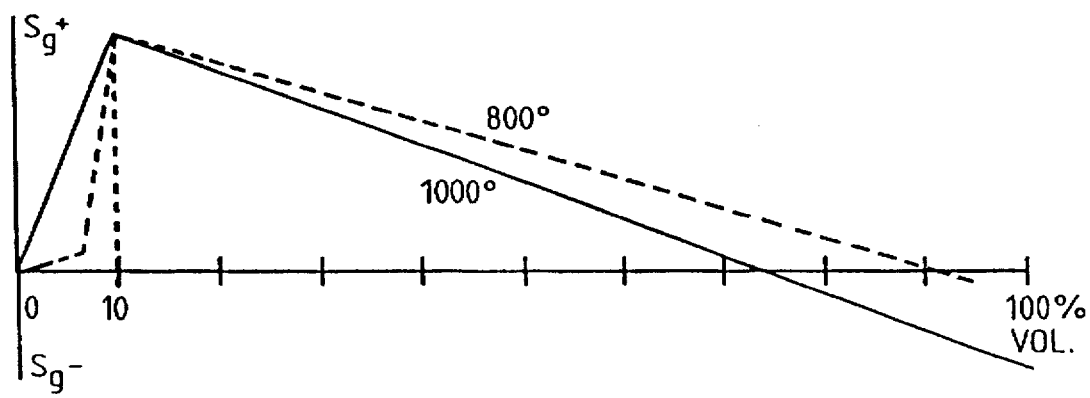
FIG. 2 is a graph showing the responses of the catalytic transducer for a volume concentration of methane varying between 0 and 100% for temperatures of 800° C. and 1,000° C.

FIG. 2 shows the response of the platinum filament during an experiment with various concentrations of methane and for operating temperatures of 800° C. (dashed line) and 1,000° C. (full line).

Beyond the stoichiometric concentration (around 10%), the response of the filament is due to antagonistic parameters: the oxidation of the gas, which contributes heat but which is reduced as the concentration of methane increases, and the conductivity of the mixture, which increases with the concentration of methane but which takes away heat. The quantities of gas oxidized at the two temperatures are practically identical above the stoichiometric concentration, but the thermal conductivity causes greater heat losses at 1,000° C. than at 800° C. This explains why the 800° response signal is above the 1,000° C. response signal for high concentrations.

Accordingly, $S_g=S_{(1000°)}-S_{(800°)}$ becomes negative for concentrations above the stoichiometric concentration. This resolves the doubt in respect of the measured volume concentration.

In a methane meter, which normally gives the volume concentration up to 5% vol, a strongly negative signal (i.e. a negative signal that is clearly not the result of a slight loss of adjustment) therefore represents a concentration above the stoichiometric concentration and is converted into a response signal showing that the volume concentration is greater than the full scale volume concentration.

If the gases concerned are known and have highly different (in terms of temperature) response curves, it is possible to name the gas whose volume concentration is measured by the above technique with multiple constant temperature phases.

Figure 3:
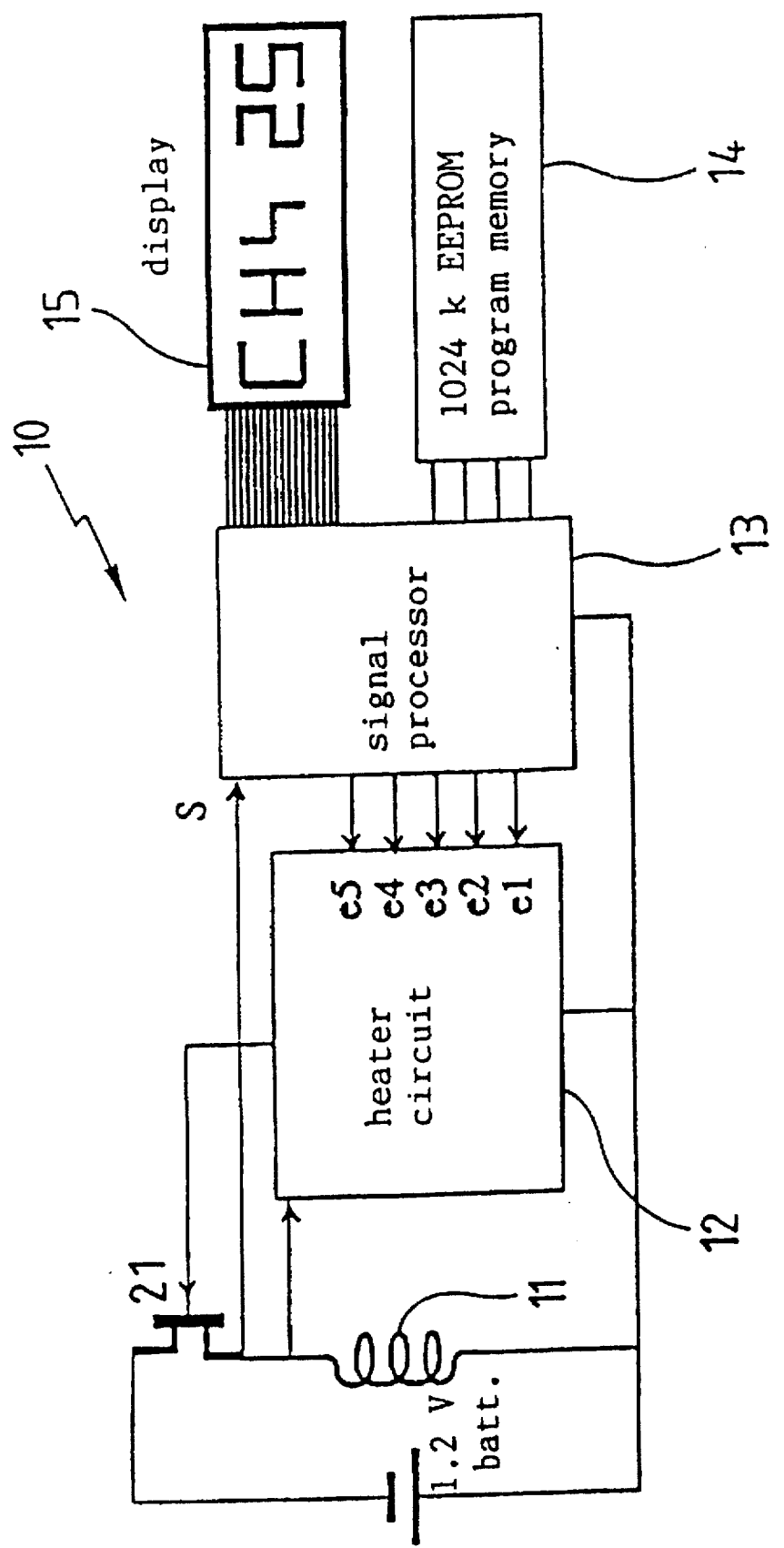
FIG. 3 is a simplified block diagram of an electronic device for implementing the method.

FIG. 3 shows the electronic circuit of a device 10 used for three applications described below (only the program differs from one application to another).

The transducer is a pure platinum filament 11 with a diameter of 80 μm formed into a coil with 11 turns and having a diameter of 0.2 mm and a length of 2 mm.

A heater circuit 12 operates a current valve 21 so that there flows in the filament only the heating current needed to maintain it at a constant operating temperature, selected by logic states applied to its inputs e1, e2, e3, e4 and e5, for example as shown in the following table:

| e5 | e4 | e3 | e2 | e1 | Heating temperature |
|---|---|---|---|---|---|
| 0 | 0 | 0 | 0 | 0 | Heating off |
| 0 | 0 | 0 | 0 | 1 | T1 |
| 0 | 0 | 0 | 1 | 1 | T2 |
| 0 | 0 | 1 | 1 | 1 | T3 |
| 0 | 1 | 1 | 1 | 1 | T4 |
| 1 | 1 | 1 | 1 | 1 | T5 |

The prototype instrument described here has, rather than the six temperature thresholds mentioned above, the following five temperature thresholds:

T1=100° C.

T2=200° C.

T3=500° C.
T4=800° C.
T5=1,000° C.

A signal processor 13 (such as a TEXAS INSTRUMENTS TSS400S) controls the steps of the method:

it commands and times the various constant temperature phases, it measures the response signals of the filament, in this example the potential differences at its terminals, it carries out the calculations, it gives the result in the form required by the application: usually % vol or % L.E.L. (Lower Explosion Limit).

The program and the various constants are stored in an EEPROM 14.

The results are displayed on a display 15.

Figure 4:
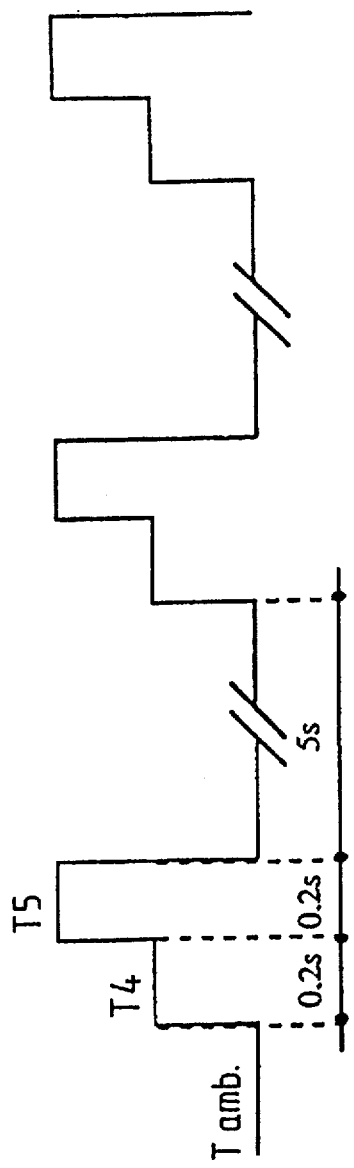
FIG. 4 is a timing diagram showing a temperature cycle applied to the transducer with two constant temperature phases, for measuring the concentration of methane, for example.

FIG. 4 shows the temperature cycle applied to the catalytic transducer when only one oxidizable gas is likely to be present in the gaseous medium to be characterized: it has two increasing constant temperature phases, of very short duration (about 0.2 s) followed by an "off" phase at room temperature and of greater duration (5 s in this example but possibly shorter if required; an "off" phase of only 2.5 s may suffice if quasi-continuous measurement is required).

In the case of methane, the lower threshold temperature and the upper threshold temperature for the temperature range in question are chosen as 800° C. and 1,000° C.

For determination of the methane concentration with resolution of doubt (methane meter), the following procedure is employed:

M1—heat filament to 800° C. for 0.2 s, measure and capture value of signal S4,

M2—heat filament to 1,000° C. for 0.2 s, measure and capture value of signal S5, M3—stop heating, M4—(if simplified calculation method chosen) calculate $d5=(S5-S4-Ct\ 5)$ and compare with a slightly negative value a, M5—if $d5>a$, calculate volume concentration from an expression of the type $A.B.d5$ where A is a sensitivity coefficient allowing for the sensitivity of the filament and B is a coefficient whereby the measured value is given in the units chosen for the application: % vol or % L.E.L.; coefficients A and B are calculated and stored by the instrument after calibration using a reference mixture, M5'—if $d5<a$, display a high methane concentration signal, M6—wait (for 5 s for example) and return to step M1.

Figure 5:
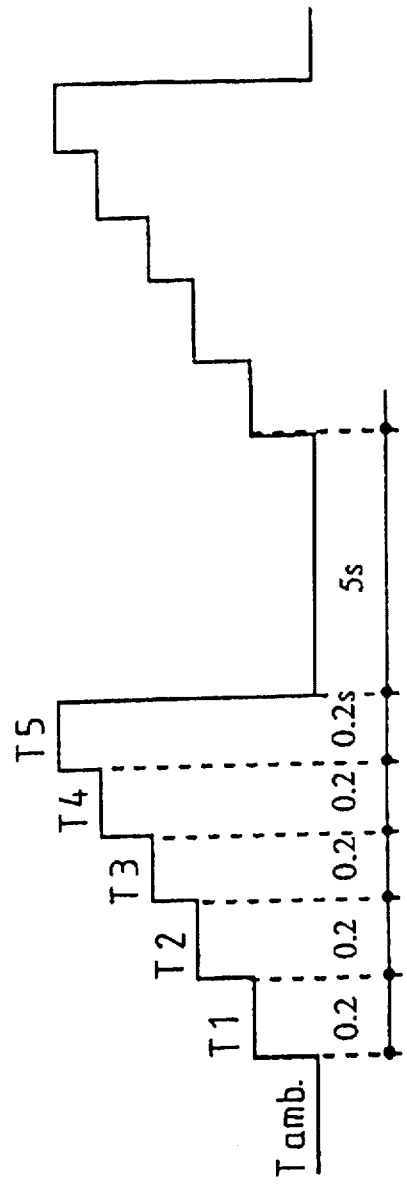
FIG. 5 is a timing diagram showing a temperature cycle applied to the transducer with five constant temperature phases, for an explosion meter application, for example.

To use the catalytic transducer as an explosion meter, the following procedure is adopted (see FIG. 5):

E1—heat filament to T1=100° C. for 0.2 s, measure and capture value of signal S1, E2—heat filament to T2=200° C. for 0.2 s, measure and capture value of signal S2, E3—heat filament to T3=500° C. for 0.2 s, measure and capture value of signal S3, E4—heat filament to T4=800° C. for 0.2 s, measure and capture value of signal S4, E5—heat filament to T5=1,000° C. for 0.2 s, measure and capture value of signal S5, E6—stop heating, E7—(using the second calculation method, for example) calculate the following terms:

$d'4=S5-K4.S4$
$d'3=S4-K3.S3$
$d'2=S3-K2.S2$
$d'1=S2-K1.S1$ in which K4 through K1 are constants (see above) specific to each temperature range, E8—select largest value $d'n$ of values $d'$ calculated in step E7, E9—calculate volume concentration using the law $d'n.An.Bn$ where An and Bn are values of coefficients Ai and Bi (see above with reference to step M5, determined for the i temperature ranges in question) for the highest value i of the values $d'i$, and display this volume concentration, E10—wait (5 s) and return to step E1.

If the filament is to be used as a selective methane meter with resolving of doubt (i.e. capable of identifying methane and measuring the methane concentration) the procedure adopted is as follows:

MS1–MS7 same as E1 through E7,

MS8—compare $d'4$ to a threshold value a (slightly negative),

MS9—if $d'4<a$, display an excess methane signal,

MS9'—if $d'4>a$ and if $d'4$ is the greatest of the values $d'i$, calculate and display as in step E9 above taking n=4, MS9"—if $d'4>a$ and if $d'4$ is not the greatest value, display nothing or calculate and display the global volume concentration as defined in steps E8 and E9, MS10—see E10.

For example, in the case of the filament as defined above:

between T1 and T2: K1=0.75
between T2 and T3: K2=0.75
between T3 and T4: K3=0.88
between T4 and T5: K4=1

The invention is naturally not restricted to a filament type transducer (i.e. a transducer including a resistive element which heats its catalytic surface to the required temperature by the JOULE effect): the transducer can be heated indirectly by a resistive element (or any other form of heating element) which heats it or is near it.

It goes without saying that the foregoing description has been given by way of non-limiting example only and that numerous variants thereof can be put forward by one skilled in the art without departing from the scope of the invention.

There is claimed:

1. A method of detecting one of a plurality of known oxidizable gases in a gaseous medium based on air, the method comprising the steps of:

placing a single catalytic transducer in said gaseous medium;

heating said single catalytic transducer to a first set threshold temperature at which said oxidizable gas is substantially not oxidized;

capturing a first value of a parameter characteristic of an output signal of said single catalytic transducer heated to said first set threshold temperature;

heating said single catalytic transducer to a second set threshold temperature at which said oxidizable gas in contact with said single catalytic transducer oxidizes substantially, said second set threshold temperature and said first set threshold temperature defining a temperature range;

capturing a second value of a parameter characteristic of an output signal of said single catalytic transducer heated to said second set threshold temperature;

using a set law to obtain a response signal representative of a characteristic of said gaseous medium produced from the difference between said second and first values of said parameters, said set law defining a value representative of a characteristic of the type, quantity, and content of said oxidizable gas actually oxidized during heating at said second set threshold temperature; and cooling said single catalytic transducer to a temperature below said first set threshold temperature to monitor said gaseous medium for said oxidizable gas.

2. A method according to claim 1 wherein said step of placing said single catalytic transducer further comprises the step of placing a single catalytic transducer having a resistive element in said gaseous medium; and said steps of heating said single catalytic transducer further comprise application of an electric current to said resistive element.

3. A method according to claim 1 wherein said step of heating said single catalytic transducer to said first set threshold temperature further comprises the step of choosing a first set threshold temperature close to a temperature above which said oxidizable gas begins to oxidize.

4. A method according to claim 1 wherein said step of placing said single catalytic transducer further comprises the step of placing a single catalytic transducer having a platinum filament; and said step of heating said single catalytic transducer to a first set threshold temperature and said step of heating said single catalytic transducer to a second set threshold temperature further comprise the step of defining said second set and first set threshold temperatures such that the differences between them is at least equal to approximately 50° C. and at most equal to approximately 300° C.

5. A method according to claim 4 wherein said step of placing said single catalytic transducer further comprises the step of placing a single catalytic transducer having a platinum filament; and said step of defining said second set and first set threshold temperatures further comprises the step of defining said second set and first set threshold temperatures such that the difference between them is at most equal to approximately 200° C.

6. A method as claimed in claim 5 wherein said one of said plurality of known oxidizable gases is chosen from the group consisting of methane and ethylene and further wherein said step of heating said single catalytic transducer to said first set threshold temperature further comprises the step of heating said single catalytic transducer to approximately 800° C.; and said step of heating said single catalytic transducer to said second set threshold temperature further comprises heating said single catalytic transducer to approximately 1000° C.

7. A method as claimed in claim 4 wherein said one of said plurality of known oxidizable gases is chosen from the group consisting of propane, butane, and ethyl alcohol and further wherein said step of heating said single catalytic transducer to said first set threshold temperature further comprises heating said single catalytic transducer to approximately 300° C.; and said step of heating said single catalytic transducer to said second set threshold temperature further comprises heating said single catalytic transducer to approximately 600° C.

8. A method as claimed in claim 4 wherein said one of said plurality of known oxidizable gases is hydrogen and further wherein said step of heating said single catalytic transducer to said first set threshold temperature further comprises heating said single catalytic transducer to approximately 100° C.; and said step of heating said single catalytic transducer to said second set threshold temperature further comprises heating said single catalytic transducer to approximately 200° C.

9. A method according to claim 1 wherein said one of said plurality of known oxidizable gases is methane and further wherein said step of using a set law further comprises the steps of:

determining when a difference between said second and first values of said parameters is positive, said response signal being dependent on said difference; and determining when said difference is negative, said response signal being dependent on a predetermined saturation signal.

10. A method according to claim 1 further comprising the step of:

characterizing said air-based gaseous medium for at least a second oxidizable gas having an oxidation onset temperature substantially different from that of the first gas, said method further comprising the steps of:

choosing a third set threshold temperature for said second oxidizable gas at which said second oxidizable gas is substantially not oxidized;

choosing a fourth set threshold temperature for said second oxidizable gas at which said second oxidizable gas oxidizes substantially, said fourth set threshold temperature being different from said second set threshold temperature, said fourth set threshold temperature and said third set threshold temperature defining a temperature range;

heating said single catalytic transducer to said threshold temperatures in succession, in increasing order;

capturing an instantaneous value of said parameter characteristic of said output signal of said single catalytic transducer for each of said threshold temperatures; and using a set procedure to produce a global response signal from the differences between the values captured for said threshold temperatures of each gas.

11. A method according to claim 10 wherein said step of defining said temperature ranges further comprises the step of defining contiguous temperature ranges.

12. A method according to claim 10 wherein said second oxidizable gas is chosen from the group consisting of hydrogen, ethyl alcohol, butane, propane, methane, ethylene and any combination thereof, said method further comprising the steps of:

heating said single catalytic transducer successively to approximately 100° C., approximately 200° C., approximately 300° C., approximately 600° C., approximately 800° C., and approximately 1,000° C.; and deriving said global response signal from the greatest difference, allowing for a characteristic constant, between values captured for each of the ranges between said aforementioned temperatures.

13. A method according to claim 10 for identifying methane in other oxidizable gases in said gaseous medium, wherein said step of heating said single catalytic transducer further comprises:

heating said single catalytic transducer successively to approximately 100° C., approximately 200° C., approximately 300° C., approximately 600° C., approximately 800° C., and approximately 1,000° C.; and producing said global response signal from the difference, allowing for a characteristic constant, between the values obtained for 1000° C. and 800° C., respectively, when said difference is negative, or is greater than the differences obtained for the other temperature ranges.

14. A method of detecting and quantitatively determining more than one known oxidizable gas in a gaseous medium based on air having oxidation onset temperatures substantially different from each other, said method comprising the steps of:

placing a single catalytic transducer in said gaseous medium;

choosing a set threshold temperature, at which said oxidizable gas is substantially not oxidized, for each of said oxidizable gases to be identified;

choosing a second set threshold temperature, at which said oxidizable gas in contact with said single catalytic transducer oxidizes substantially for each of said oxidizable gases to be identified;

defining a threshold temperature range based on said second set threshold temperature and said first set threshold temperature for each of said oxidizable gases;

heating said single catalytic transducer to said threshold temperatures in succession in increasing order;

capturing an instantaneous value of a parameter characteristic of an output of said single catalytic transducer for each of said threshold temperatures;

using a set procedure to produce a global response signal from the differences between the values captured for said threshold temperature of each gas whereby identification and quantitative determination is made of each oxidizable gas present in said gaseous medium; and cooling said single catalytic transducer to a temperature below said first set threshold temperature to monitor said gaseous medium for each of said oxidizable gases.

* * * * *

UNITED STATES PATENT AND TRADEMARK OFFICE
CERTIFICATE OF CORRECTION

PATENT NO. : 5,709,792
DATED : January 20, 1998
INVENTOR(S) : Zdanevitch et al.

It is certified that error appears in the above-identified patent and that said Letters Patent is hereby corrected as shown below:

Column 2, line 48, kindly delete "0 234 258" and insert

---- 0 458 058 ----.

Column 3, line 24, kindly delete "said" and insert ---- the ----.

Signed and Sealed this

Sixteenth Day of March, 1999

Attest:

Q. TODD DICKINSON

Attesting Officer     Acting Commissioner of Patents and Trademarks